(12) United States Patent
Kwon et al.

(10) Patent No.: US 11,406,358 B2
(45) Date of Patent: Aug. 9, 2022

(54) ULTRASONIC PROBE

(71) Applicant: SAMSUNG MEDISON CO., LTD., Gangwon-do (KR)

(72) Inventors: Gi Han Kwon, Yongin-si (KR); Won-Soon Hwang, Hanam-si (KR)

(73) Assignee: SAMSUNG MEDISON CO., LTD., Gangwon-Do (KR)

(*) Notice: Subject to any disclaimer, the term of this patent is extended or adjusted under 35 U.S.C. 154(b) by 509 days.

(21) Appl. No.: 16/078,979

(22) PCT Filed: Dec. 13, 2016

(86) PCT No.: PCT/KR2016/014598
§ 371 (c)(1),
(2) Date: Aug. 22, 2018

(87) PCT Pub. No.: WO2017/146364
PCT Pub. Date: Aug. 31, 2017

(65) Prior Publication Data
US 2019/0059853 A1   Feb. 28, 2019

(30) Foreign Application Priority Data
Feb. 22, 2016 (KR) .................. 10-2016-0020415

(51) Int. Cl.
*A61B 8/00* (2006.01)
*G01S 15/89* (2006.01)
(Continued)

(52) U.S. Cl.
CPC .......... *A61B 8/4444* (2013.01); *A61B 8/4483* (2013.01); *B06B 1/067* (2013.01);
(Continued)

(58) Field of Classification Search
CPC ..... A61B 8/4444; A61B 8/4483; B06B 1/067; B06B 2201/76; G01S 15/8934; G01S 7/52082; H01L 41/1876
See application file for complete search history.

(56) References Cited

U.S. PATENT DOCUMENTS

| 2005/0165313 A1 | 7/2005 | Byron et al. |
| 2014/0208853 A1 | 7/2014 | Onishi |
| 2014/0211587 A1 | 7/2014 | Kiyose |

FOREIGN PATENT DOCUMENTS

| JP | H09-055997 A | 2/1997 |
| JP | H09-075345 A | 3/1997 |

(Continued)

OTHER PUBLICATIONS

Extended European Search Report dated Jul. 30, 2019 issued in European Patent Application No. 16891766.4.
(Continued)

*Primary Examiner* — Michael T Rozanski
(74) *Attorney, Agent, or Firm* — Morgan, Lewis & Bockius LLP

(57) ABSTRACT

Provided is an ultrasonic probe having a buffer structure capable of preventing internal components from being damaged by an external impact. The ultrasonic probe includes a transducer module transmitting and receiving an ultrasonic wave, a case which has an opened one side and is configured to accommodate the transducer module, a lens provided at the one side of the case, and a protective member accommodated in the case and positioned to face at least one surface of the transducer module, wherein the protective member protrudes further forward compared to the piezoelectric layer.

15 Claims, 12 Drawing Sheets

(51) Int. Cl.
*G01S 7/52* (2006.01)
*B06B 1/06* (2006.01)
*H01L 41/187* (2006.01)

(52) U.S. Cl.
CPC ...... *G01S 7/52082* (2013.01); *G01S 15/8934* (2013.01); *B06B 2201/76* (2013.01); *H01L 41/1876* (2013.01)

(56) References Cited

FOREIGN PATENT DOCUMENTS

| JP | H10-005227 A | 1/1998 |
| JP | 2012-085723 A | 5/2012 |
| JP | 2014-146885 A | 8/2014 |

OTHER PUBLICATIONS

Written Opinion and International Search Report dated Mar. 20, 2017 issued in International Patent Application No. PCT/KR2016/014598 (with English translation).

[Fig. 1]
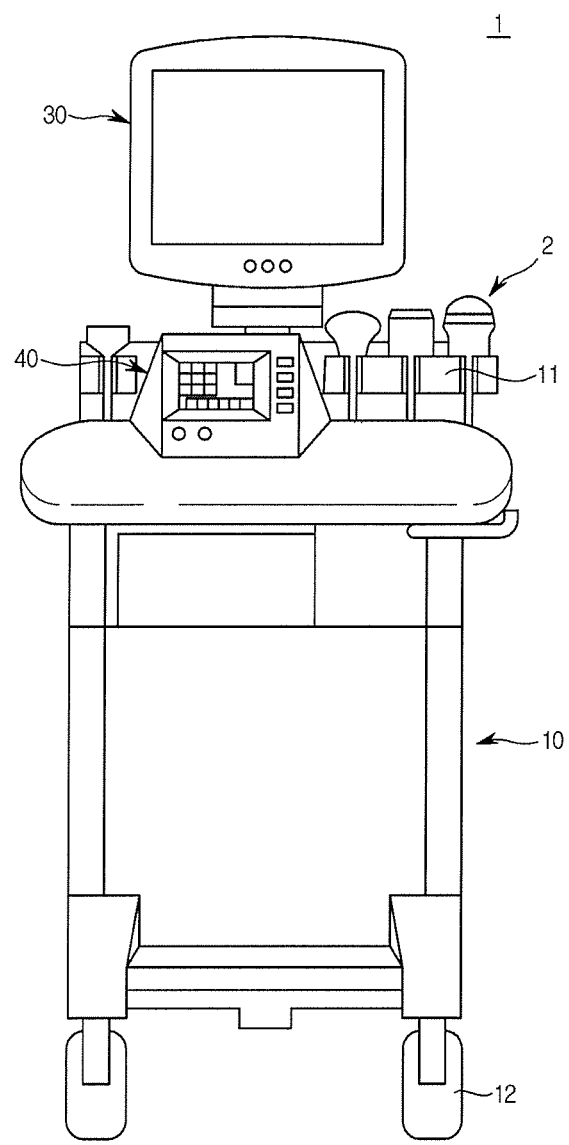

[Fig. 2]
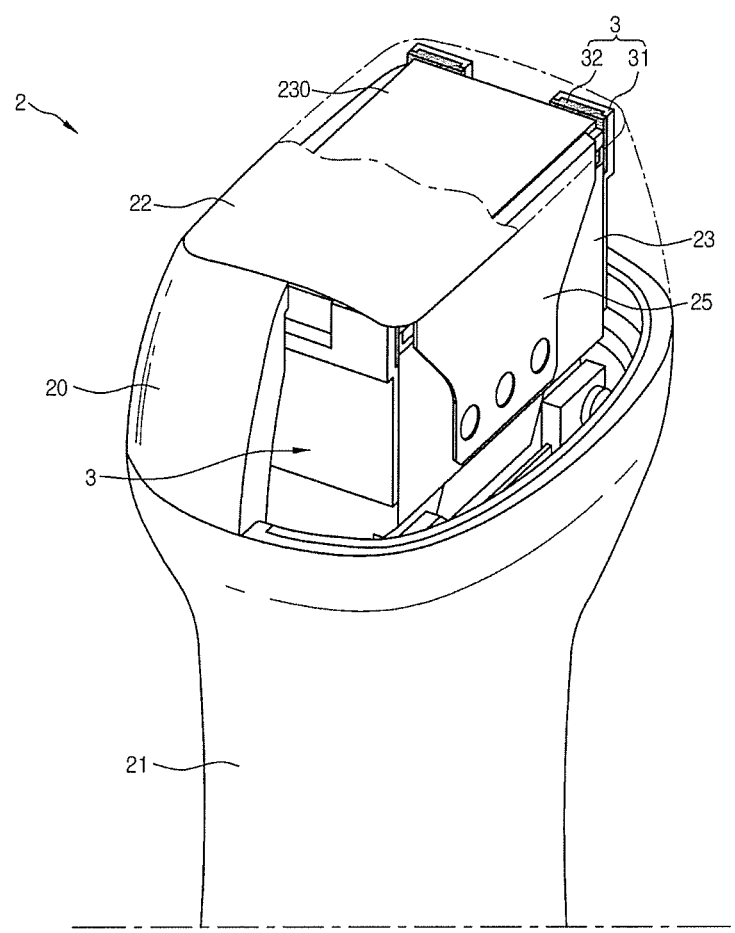

[Fig. 3]
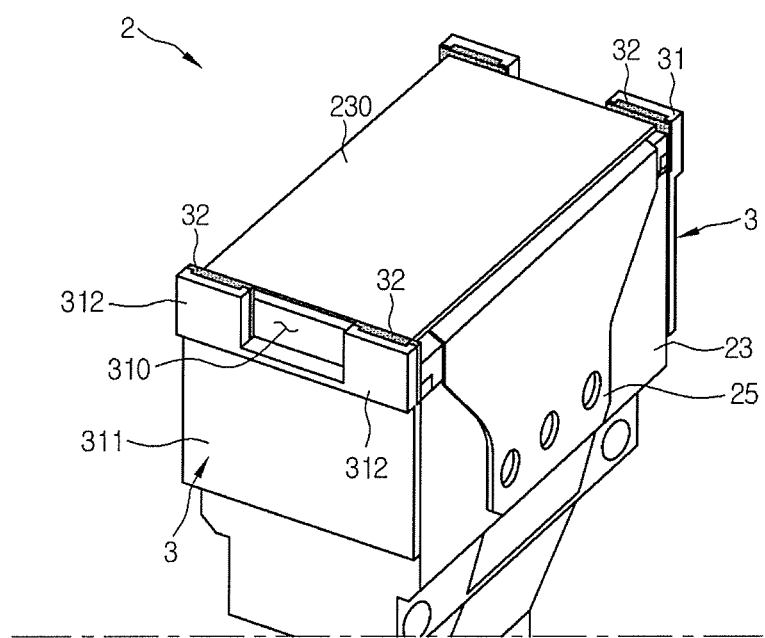

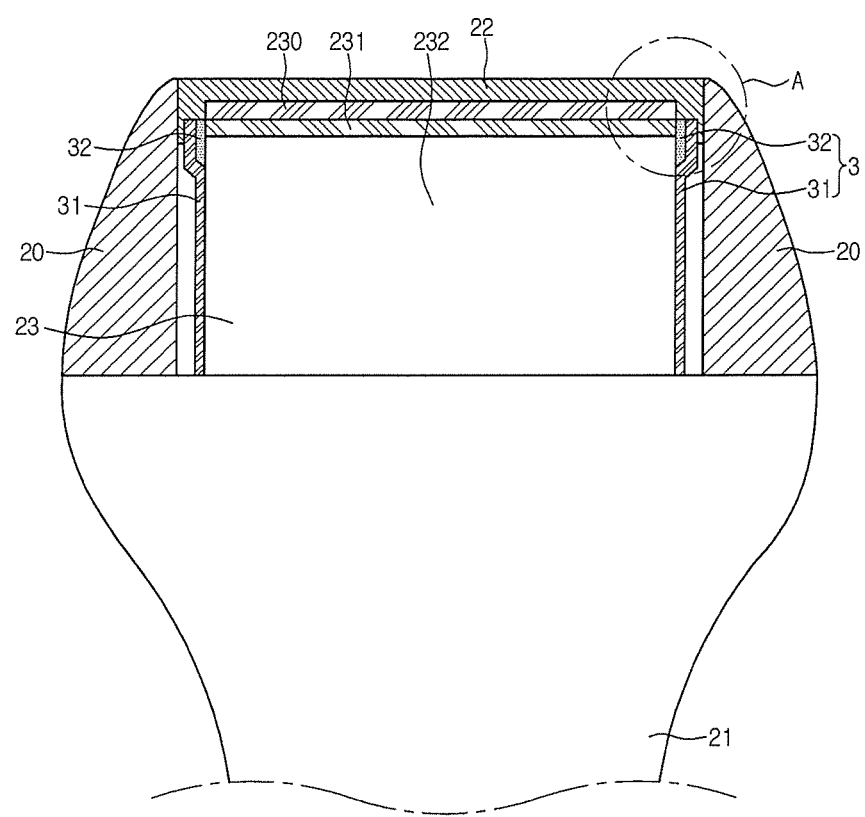
[Fig. 4a]

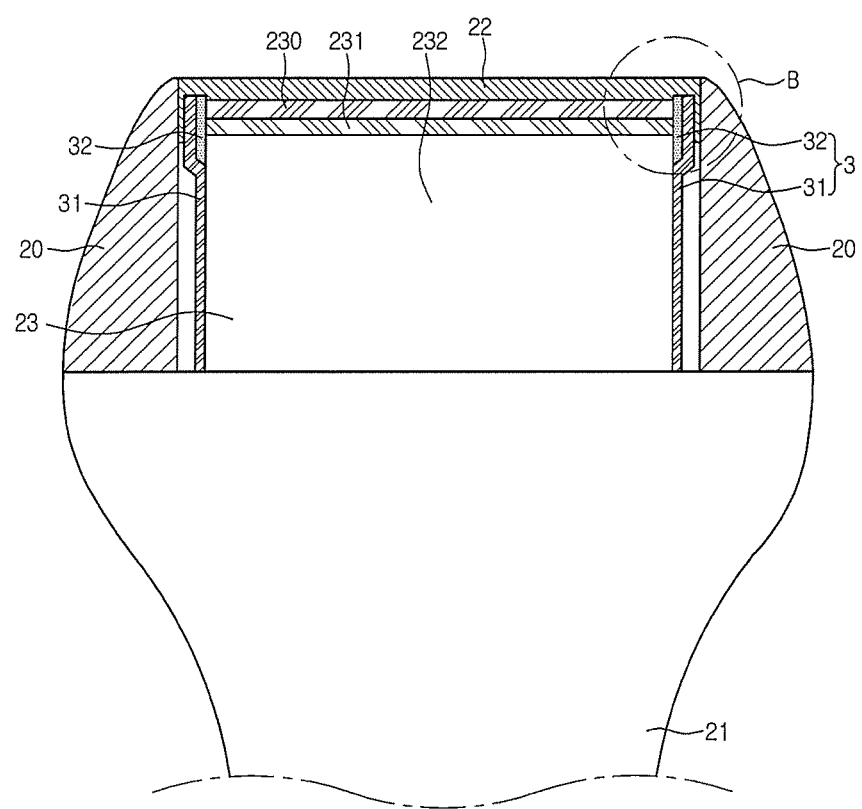
[Fig. 4b]

[Fig. 5a]
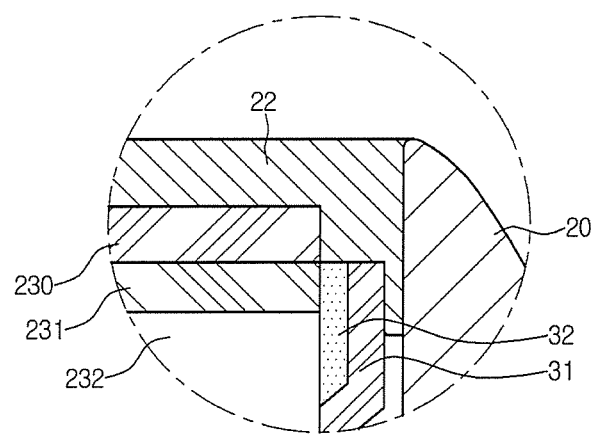

[Fig. 5b]
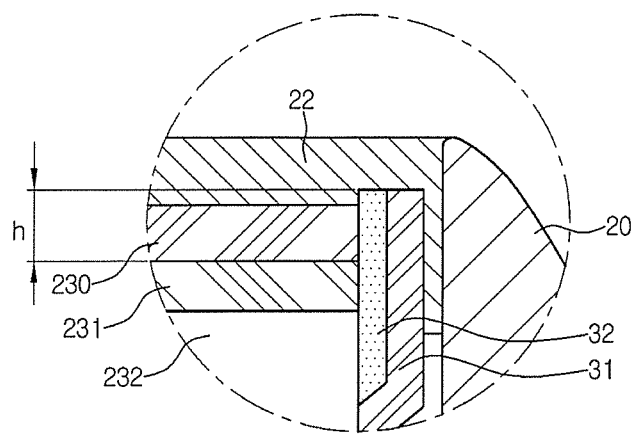

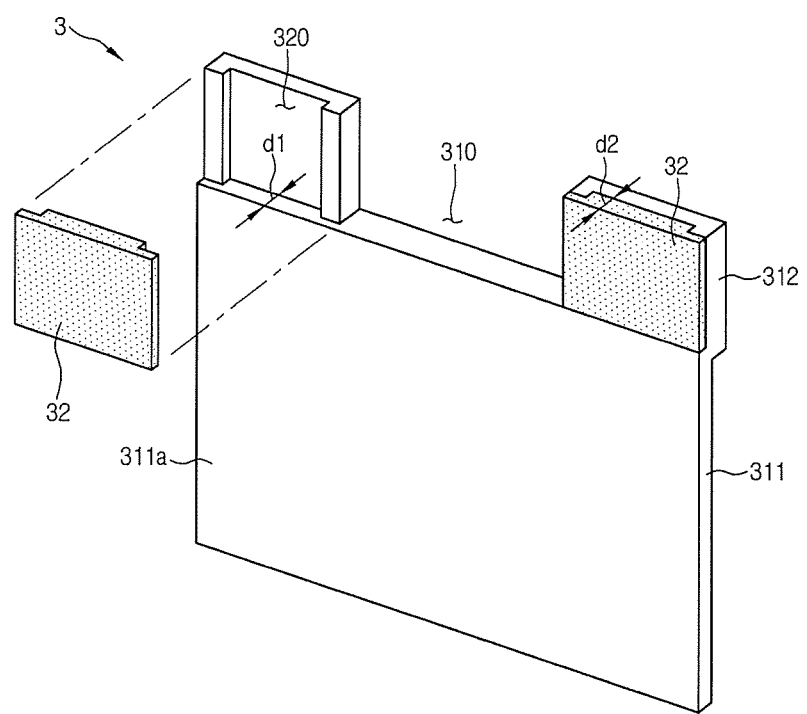
[Fig. 6]

[Fig. 7]
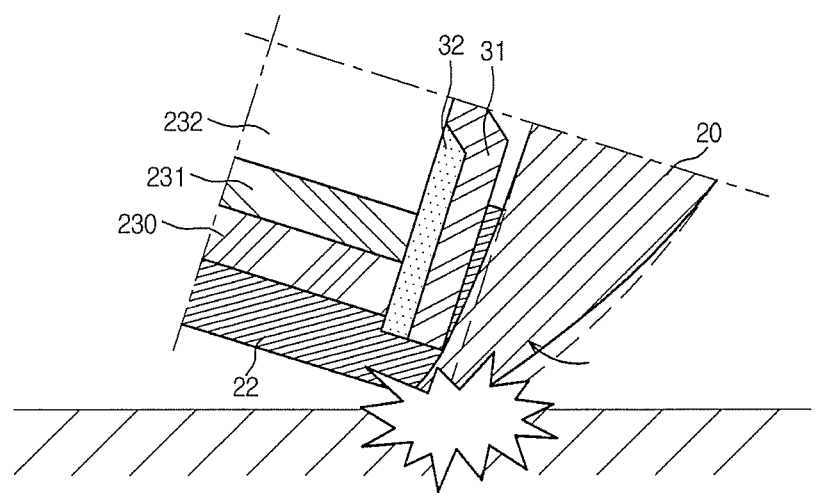

[Fig. 8]
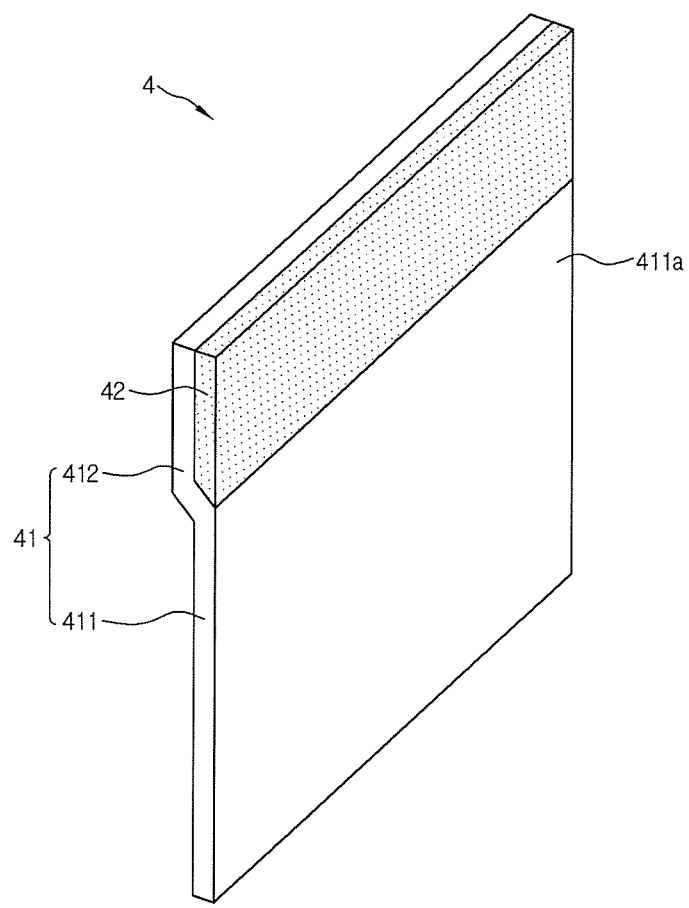

[Fig. 9]
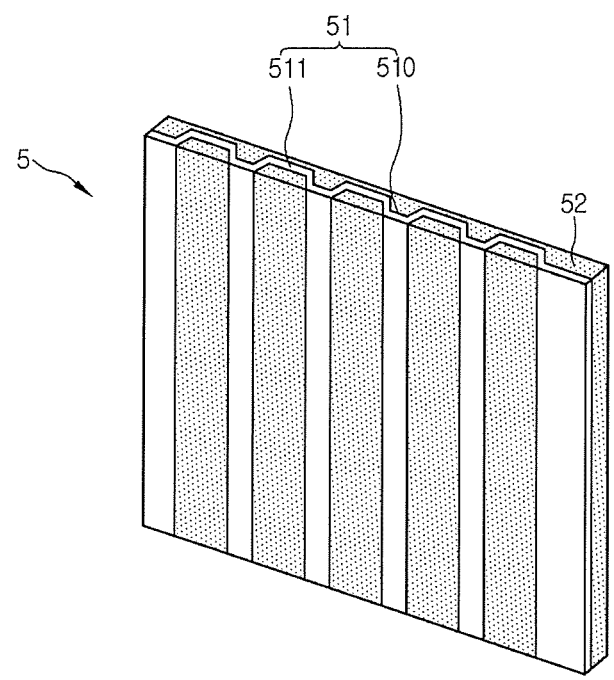

[Fig. 10]
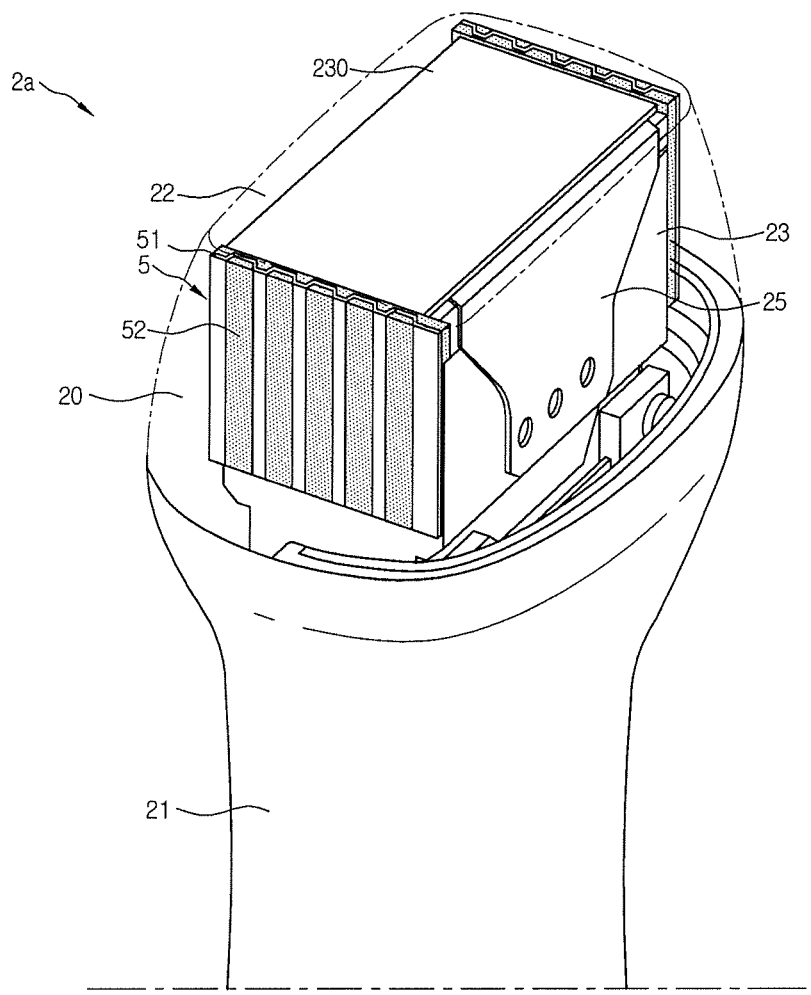

ULTRASONIC PROBE

CROSS REFERENCE

This patent application is the U.S. National Phase under 35 U.S.C. § 371 of International Application No. PCT/KR2016/014598, filed on Dec. 13, 2016, which claims the benefit of Korean Patent Application No. 10-2016-0020415, filed on Feb. 22, 2016, the entire contents of each are hereby incorporated by reference.

TECHNICAL FIELD

The present invention relates to an ultrasonic probe for acquiring an ultrasonic image.

BACKGROUND ART

An ultrasonic imagining device is a device which irradiates an ultrasonic wave onto a target part inside a subject from a body surface of the subject and non-invasively acquires a tomogram of a soft tissue or an image of blood flow by using information on a reflected ultrasonic signal (ultrasonic echo signal).

The ultrasonic imaging device has advantages such as a smaller size and a lower price, a real-time display, and high safety without radiation exposure in comparison with other imaging diagnostic devices such as an X-ray diagnostic device, an X-ray computerized tomography (CT) scanner, a magnetic resonance image (MRI) scanner, and a nuclear medicine diagnostic device. Thus, the ultrasonic diagnostic device has been widely used in diagnosis in cardiac, abdominal, urologic, and obstetric fields.

DISCLOSURE

Technical Problem

According to an exemplary embodiment, the present invention is directed to providing an ultrasonic probe having a buffer structure, capable of preventing internal components from being damaged by an external impact.

Technical Solution

An ultrasonic probe according to an aspect of the present invention includes: a transducer module including a piezoelectric layer configured to generate an ultrasonic wave; a case which has an opened one side and is configured to accommodate the transducer module; a lens provided at the one side of the case; and a protective member accommodated in the case and positioned to face at least one surface of the transducer module, wherein the protective member protrudes further forward compared to the piezoelectric layer so as to protect the piezoelectric layer from an external impact.

The protective member may include an impact blocking member provided to protrude further forward compared to the transducer module and an impact absorbing member disposed between the impact blocking member and the transducer module to absorb an impact transmitted to the impact blocking member.

The impact blocking member may include a first impact blocking portion and a second impact blocking portion extending in a stepped manner from the first impact blocking portion.

The impact absorbing member may be positioned between the second impact blocking portion and the transducer module.

The second impact blocking portion may extend forward from the first impact blocking portion.

A plurality of second impact blocking portions may be provided to extend.

Two second impact blocking portions may be provided and positioned at a left side and a right side of the transducer module.

A length from one end of any one second impact blocking portion of the two second impact blocking portions to the other end of the other one may be the same as a left-and-right length of one side surface of the transducer module.

A single second impact blocking portion may be provided and extend forward in a stepped manner from the first impact blocking portion.

The impact absorbing member may be positioned between the second impact blocking portion and the transducer module.

The impact blocking member may be provided such that a concave portion and a convex portion are alternately formed.

The concave portion and the convex portion may be provided to extend in a forward and backward direction of the transducer module.

The impact absorbing member may be positioned in a space formed by the concave portion and the convex portion.

The impact absorbing member may include at least one selected from silicon rubber, polythene (PE), a polymer, an elastomer, and cellulose.

The impact blocking member may be made of a metal or nonmetal material having a tensile modulus of 2 GPa or more.

An ultrasonic probe according to an exemplary embodiment is an ultrasonic probe configured to transmit and receive an ultrasonic wave to acquire an image inside a subject, the ultrasonic probe including: a transducer module including a piezoelectric layer configured to generate an ultrasonic wave; an impact blocking member provided on at least side surface of the transducer module and provided to have the same height as the piezoelectric layer, or to protrude forward; and an impact absorbing member disposed between the impact blocking member and the transducer module to absorb an impact transmitted to the impact blocking member.

The impact blocking member may include a stepped portion, and the impact absorbing member may be positioned between the stepped portion and the transducer module.

The stepped portion is positioned in front of the transducer nodule.

The impact blocking member may be provided to have the same width as one side surface of the transducer module.

A lens may be provided in front of the transducer module to come into contact with the subject, and the impact blocking member may have rigidity higher than rigidity of the lens.

Advantageous Effects

Since an ultrasonic probe according to an aspect of the present invention has a buffer structure, the ultrasonic probe can absorb an external impact.

In addition, internal components provided in the ultrasonic probe can be prevented from being damaged.

Furthermore, quality of an ultrasonic image can be prevented from being reduced by the external impact.

DESCRIPTION OF DRAWINGS

FIG. 1 is a view illustrating an ultrasonic imaging device according to an exemplary embodiment.

FIG. 2 is a view illustrating a portion of an ultrasonic probe according to the exemplary embodiment.

FIG. 3 is an internal view illustrating the ultrasonic probe according to the exemplary embodiment.

FIG. 4A is a cross-sectional view illustrating the ultrasonic probe according to the exemplary embodiment.

FIG. 4B is a cross-sectional view illustrating an ultrasonic probe according to a modified example.

FIG. 5A is a view illustrating portion A of FIG. 4A.

FIG. 5B is a view illustrating portion B of FIG. 4B.

FIG. 6 is a view illustrating a protective member provided in an ultrasonic probe according to an exemplary embodiment.

FIG. 7 is a view illustrating a state when an external impact is applied to the ultrasonic probe according to the exemplary embodiment.

FIG. 8 is a view illustrating a protective member according to another exemplary embodiment.

FIG. 9 and FIG. 10 are views illustrating a protective member according to another exemplary embodiment.

FIG. 10 is an internal view illustrating an ultrasonic view including the protective member according to another exemplary embodiment.

MODES OF THE INVENTION

Hereinafter, an ultrasonic probe according to an exemplary embodiment will be described in detail with reference to the accompanying drawings.

FIG. 1 is a view illustrating an ultrasonic imaging device according to an exemplary embodiment.

Referring to FIG. 1, an ultrasonic imaging device 1 according to an exemplary embodiment includes a main body 10 and an ultrasonic probe 2 configured to transmit an ultrasonic signal to a subject to be diagnosed and receive a signal reflected from the subject. The ultrasonic probe 2 may be connected to the main body 10 through a cable.

A display 30 may be provided in the main body 10 to display a diagnosis result obtained through a received ultrasonic signal. The display 30 may display an application related to operation of the ultrasonic imaging device 1. In an example, the display 30 may display ultrasonic images acquired during an ultrasonic diagnosis process or items related to the operation of the ultrasonic imaging device 1.

The display 30 may be implemented as a cathode ray tube (CRT) or a liquid crystal display (LCD). A plurality of displays 30 may be provided. When the plurality of displays 30 are provided, the displays 30 may include a main display and a sub-display. In an example, the main display may display the ultrasonic images acquired during the ultrasonic diagnosis process. The sub-display may display the items related to the operation of the ultrasonic imaging device.

An input unit 40 may be provided in the main body 10. The input unit 40 may be provided in the form of a keyboard, a foot switch, a foot pedal, or the like. When the input unit 40 is the keyboard, the keyboard may be provided on an upper portion of the main body 10. When the input unit 40 is the foot switch or the foot pedal, the foot switch or the foot pedal may be provided on a lower portion of the main body 10. A sonographer may control operation of the ultrasonic imaging device 1 through the input unit 40.

The probe 2 may be hung on the main body 10 through a holder 11. When the sonographer does not use the ultrasonic imaging device 1, the sonographer may hang and store the probe 2 on the holder 11.

A shifter 12 may be provided in the main body 10 so as to move the ultrasonic imaging device 1. The shifter 12 may include a plurality of castors provided on a bottom surface of the main body 10. The castors may be aligned to move the main body 10 in a specific direction, may be provided so as to be freely movable in any direction, or may be locked so as to stop at a specific position.

FIG. 2 is a view illustrating a portion of the ultrasonic probe according to the exemplary embodiment. FIG. 3 is an internal view illustrating the ultrasonic probe according to the exemplary embodiment. FIG. 4A is a cross-sectional view illustrating the ultrasonic probe according to the exemplary embodiment. FIG. 4B is a cross-sectional view illustrating an ultrasonic probe according to a modified example. FIG. 5A is a view illustrating portion A of FIG. 4A. FIG. 5B is a view illustrating portion B of FIG. 4B.

Referring to FIGS. 2 to 5B, in order to acquire an ultrasonic image of a subject, the ultrasonic probe 2 transmits an ultrasonic signal to the subject and receives an ultrasonic signal reflected from the subject to transmit the received ultrasonic signal to a controller.

The ultrasonic probe 2 includes a case 20 which has an opened one side and is configured to accommodate a transducer module 23, a handle 21 mounted at one side of the case 20, and a lens 22 provided in front of the transducer module 23 to come into direct contact with a subject to be diagnosed. The lens 22 may be mounted at one side of the case 20.

The transducer module 23 provided in the ultrasonic probe 2 includes a piezoelectric layer 231 configured to perform interconversion on an electric signal and an acoustic signal through vibration of a piezoelectric material. The piezoelectric layer 231 is configured to generate an ultrasonic wave by using a resonance phenomenon. The piezoelectric layer 231 may be made of lead zirconate titanate (PZT) ceramic, a single crystal made of a solid solution of lead zinc niobate and lead titanate (PZNT), a single crystal made of a solid solution of lead magnesium niobate and lead titanate (PZMT), or the like.

Meanwhile, electrodes (not shown) respectively corresponding to a positive electrode and a negative electrode may be provided in a front and a rear of the piezoelectric layer 231. The electrodes may be made of a high conductive material such as gold, silver, or copper. The electrode corresponding to the positive electrode and the electrode corresponding to the negative electrode may be electrically connected to a flexible printed circuit board (PCB) 25 to receive electricity.

The transducer module 23 provided in the ultrasonic probe 2 may include a sound absorption layer 232. The sound absorption layer 232 may be positioned to the rear of the piezoelectric layer 231. The sound absorption layer 232 may suppress free vibration of the piezoelectric layer 231 to reduce a pulse width of an ultrasonic wave and may block an ultrasonic wave from being unnecessarily transmitted rearward from the piezoelectric layer 231 to prevent an ultrasonic image from being distorted. The sound absorption layer 232 may be made of a material which includes rubber to which an epoxy resin, a tungsten powder, and the like are added.

In addition, the transducer module 23 includes an acoustic matching layer 230. The acoustic matching layer 230 may function to reduce acoustic impedance between the piezoelectric layer 231 and a subject such that an ultrasound wave generated in the piezoelectric layer 231 is transmitted to the subject as much as possible. The acoustic matching layer 230 may be positioned to the front of the piezoelectric layer 231. The acoustic matching layer 230 may be provided to have a median value between acoustic impedance of the piezoelectric layer 231 and acoustic impedance of the subject. The acoustic matching layer 230 may be made of a glass or resin material. A plurality of acoustic matching layers 230 made of different materials may be stacked and provided such that acoustic impedance is gradually changed from the piezoelectric layer 231 to the subject.

The transducer module 23 may be accommodated in the case 20, and the lens 22 may be disposed in front of the transducer module 23. The lens 22 disposed in front of the transducer module 23 may focus the ultrasonic wave generated in the piezoelectric layer 231. The lens 22 may be made of a material such as silicon or rubber, which has an acoustic impedance value similar to the acoustic impedance of the subject. The lens 22 may be of a convex type which has a central portion formed in a convex surface or of a linear type which has a flat surface.

A protective member 3 may be provided in the case 20 to protect the transducer module 23 from an external impact. The protective member 3 may be provided on at least one side of the transducer module 23. Since the transducer module 23 is protected by the protective member 3, an external impact applied to the ultrasonic probe 2 may not be directly transmitted to the transducer module 23.

The protective member 3 may be provided at each of two opposite sides of the transducer module 23. The protective member 3 may be installed to cover side surfaces of the transducer module 23.

When a user grasps the handle 21 to use the ultrasonic probe 2, the user may drop the ultrasonic probe 2, or when the ultrasonic probe 2 is used, the ultrasonic probe 2 may strongly collide with other objects. When the ultrasonic probe 2 collides with external objects, the transducer module 23 positioned in the ultrasonic probe 2 may be damaged by an external impact.

In particular, the lens 22 made of a soft material including silicon, rubber, and the like is positioned on a front surface of the ultrasonic probe 2. The lens 22 positioned in front of the transducer module 23 is generally made of a soft material including silicon, rubber, and the like. Therefore, the lens 22 may not properly protect the transducer module 23 positioned in the ultrasonic probe 2 from an external impact. Therefore, the ultrasonic probe 2 may be more vulnerable to an external impact transmitted through a front surface of the ultrasonic probe 2, on which the lens 22 is positioned, or a corner at which the case 20 and the lens 22 are connected.

The piezoelectric layer 231 may be formed in the form of an air kerf to maximize ultrasonic wave generation performance. The piezoelectric layer 231 formed in the form of the air kerf is vulnerable to an external impact. Therefore, when the piezoelectric layer 231 is formed in the form of the air kerf, the transducer module 23 may be more easily damaged by an external impact.

In the case of the present invention, since the protective member 3 is provided at each of the sides of the transducer module 23, an external impact applied to the front surface or the corner of the ultrasonic probe 2 may not transmitted to the transducer module 23 by the protective member 3 or may be absorbed by the protective member 3 and thus be transmitted to the transducer module 23. As described above, the protective member 3 may be provided, thereby preventing the transducer module 23 from being damaged due to an external impact.

Referring to FIG. 4A, the protective member 3 according to the exemplary embodiment may be provided to have the same height as the piezoelectric layer 231. The piezoelectric layer 231 may be protected from an external impact by the protective member 3. In particular, an external impact transmitted through the corner of the ultrasonic probe 2 may be prevented from being transmitted to the piezoelectric layer 231.

The protective member 3 may be provided to have the same height as the piezoelectric layer 231 or may be provided to protrude slightly higher compared to the piezoelectric layer 231 and to have a lower height than the acoustic matching layer 230.

Referring to FIG. 5B, a protective member 3 according to the modified example may be provided to protrude forward by a certain height H compared to a piezoelectric layer 231. Since the protective member 3 protrudes further compared to a front surface of the piezoelectric layer 231, although an impact is applied from the outside of an ultrasonic probe 2, the impact applied from the outside may be transmitted to the protective member 3 and thus may not be directed be transmitted to the piezoelectric layer 231. The impact applied from the outside may be transmitted to the protective member 3 and be absorbed by the protective member 3, and thus, may be transmitted to a transducer module 23.

The protective member 3 may be provided to protrude further compared to an acoustic matching layer 230 or to have the same height as the acoustic matching layer 230.

Since the protective member 3 is provided to protrude further forward compared to the piezoelectric layer 231, an external impact applied to the ultrasonic probe 2 may be transmitted to the protective member 3. The transducer module 23 may be protected from an external impact by the protective member 3.

As describe above, since the protective member 3 is provided to have the same height as the piezoelectric layer 231 or to protrude further forward compared to the piezoelectric layer 231, at least one side surface of the piezoelectric layer 231 may be covered with the protective member 3. As a result, the piezoelectric layer 231 may be protected from an external impact by the protective member 3. In addition, when the protective member 3 is provided to protrude further compared to the acoustic matching layer 230, the transducer module 23 may be also protected from an external impact transmitted from a front of the ultrasonic probe 2.

FIG. 6 is a view illustrating a protective member provided in an ultrasonic probe according to an exemplary embodiment. FIG. 7 is a view illustrating a state when an external impact is applied to the ultrasonic probe according to the exemplary embodiment.

Referring to FIGS. 6 and 7, a protective member 3 according to an exemplary embodiment may include an impact blocking member 31 and an impact absorbing member 32. The impact blocking member 31 may be positioned at a side surface of a transducer module 23, and the impact absorbing member 32 may be positioned at one side of the impact blocking member 31. The impact absorbing member 32 may be positioned between the impact blocking member 31 and the transducer module 23.

The impact blocking member 31 may include a first impact blocking portion 311 disposed to a rear of the transducer module 23 and a second impact blocking 312 formed so as to be stepped with respect to the first impact blocking portion 311. As shown in FIG. 5, the second impact blocking portion 312 may be provided to further protrude from an entire surface of the transducer module 23 by a certain height h.

The second impact blocking portion 312 may be stepped so as to be far away from a side surface of the transducer module 23 compared to the first impact blocking portion 311. Therefore, a distance between the side surface of the transducer module 23 and the second impact blocking portion 312 may be longer than a distance between the side surface of the transducer module 23 and the first impact blocking portion 311 by a stepped distance d1. [73] An accommodation portion 320 configured to accommodate the impact absorbing member 32 may be provided in a space between a stepped portion of the first impact blocking portion 311 and one side surface of the second impact blocking portion 312. The second impact blocking portion 312 may be accommodated in the accommodation portion 320 to absorb an impact transmitted to the second impact blocking portion 312.

[73] A thickness d2 of the impact absorbing member 32 may be the same as the stepped length d1 of the second impact blocking portion 312. Therefore, when the impact absorbing member 32 is accommodated in the accommodation portion 320, one surface 311a of the first impact blocking portion 311 may form the same plane with one surface of the impact absorbing member 32. In some cases, the impact absorbing member 32 may be provided to further protrude toward the transducer module 23 compared to the first impact blocking portion 311.

The second impact blocking portion 312 may extend from each of a left side and a right side of the first impact blocking portion 311. Two second impact blocking portions 312 may be provided so as to be spaced apart from each other, and thus, a side surface of the transducer module 23 may be exposed through a space 310 between the second impact blocking portions 312. A plurality of second impact blocking portions 312 may be provided so as to be spaced apart from each other and to extend from the first impact blocking portion 311, thereby reducing material costs of the impact blocking member 31 and material costs of the impact absorbing member 32 mounted in the second impact blocking portion 312.

Two second impact blocking portions 312 may extend to opposite both edges of one side surface of the transducer module 23, to which the impact blocking member 31 is disposed adjacent. That is, a length from one end of any one second impact blocking portion 312 to the other end of the other second impact blocking portion 312 may be the same as a left-and-right length of the transducer module 23.

While it has been described that two second impact blocking portions 312 extend from the first impact blocking portion 311, the number of the second impact blocking portions 312 extending from the first impact blocking portion 311 is not limited to that described above. In addition, two second impact blocking portions 312 may be provided to surround the opposite edges of one side surface of the transducer module 23, to which the impact blocking member 31 is disposed to be adjacent.

The impact blocking member 31 may be made of a material having rigidity higher than that of the lens 22. The impact absorbing member 32 may be made of a material having rigidity lower than that of the lens 22. The impact absorbing member 32 may be positioned at one side of the impact blocking member 31.

The impact blocking member 31 may be made of a hard material so as to withstand an impact applied from the outside of the ultrasonic probe 2. A hard material usable as a material of the impact blocking member 31 may mean a metal or nonmetal material having a tensile modulus of 2 GPa or more as defined by a tensile test (ASTM D638) of American Society for Testing and Materials (ASTM).

The transducer module 23 may be protected by the impact blocking member 31 such that an external impact applied to the ultrasonic probe 2 is transmitted to the impact blocking member 31 rather than the transducer module 23 and the external impact is not directly transmitted to the transducer module 23. Since the impact blocking member 31 is made of a material having high rigidity, a deformation amount of the impact blocking member 31 caused by an external impact may not be great, thereby effectively preventing the external impact from being directly transmitted to the transducer module 23.

The impact absorbing member 32 may be made of a soft material so as to absorb an impact transmitted to the impact blocking member 31. A material usable as the impact absorbing member 32 means a material having a hardness (shore A) of 50 or less as defined by a hardness test (ASTM D2240) and a tensile strength of 3 MPa or less as defined by a tensile test (ASTM D412) of ASTM. A material usable as the impact absorbing member 32 may be a single material or a composite material such as silicon rubber, polythene (PE), a polymer, an elastomer, or cellulose.

The impact absorbing member 32 may absorb an impact transmitted to the impact blocking member 31. The impact transmitted to the impact blocking member 31 may be absorbed by the impact absorbing member 32 and thus may be prevented from being transmitted to the transducer module 23 through a side surface of the impact blocking member 31.

As described above, an external impact applied to the ultrasonic probe 2 may be prevented from being directly transmitted to the transducer module 23 by the impact blocking member 31, and an impact transmitted to the impact blocking member 31 may be absorbed by the impact absorbing member 32 and thus may be prevented from being transmitted to the transducer module 23 through the side surface of the impact blocking member 31.

FIG. 8 is a view illustrating a protective member according to another exemplary embodiment.

Referring to FIG. 8, a protective member 4 according to another exemplary embodiment includes an impact blocking member 41 positioned at a side surface of a transducer module 23 and an impact absorbing member 42 positioned between the impact blocking member 41 and the transducer module 23.

The impact blocking member 41 may include a first impact blocking portion 411 positioned to a rear of one side surface of the transducer module 23 and a second impact blocking portion 412 provided so as to be stepped from the first impact blocking portion 411. The second impact blocking portion 412 is provided so as to protrude by a certain height in front of the transducer module 23 similar to the protective member 3 shown in FIGS. 6 and 7.

Contents of the protective member 3 according to the exemplary embodiment shown in FIGS. 4A, 4B, 5A and 5B may be similarly applied to a material, an installation portion, and the like of the impact blocking member 41 and the impact 25 absorbing member 42. Unlike the protective member 3 according to the exemplary embodiment shown in FIGS. 4A, 4B, 5A and 5B, a single second impact blocking portion 412 as shown in FIG. 8 may be provided. The second impact blocking portion 412 may have the same width as the first impact blocking portion 411 and may be formed so as to be stepped from the first impact blocking portion 411.

The impact absorbing member 42 may be positioned in a space formed between a front end of the first impact blocking portion 411 and the second impact blocking portion 412. The impact blocking member 41 may be formed to cover the whole of one side surface of the transducer module 23.

An external impact generated at a front or a front corner of the ultrasonic probe 2 may not be directly transmitted to the transducer module 23 by the impact blocking member 41. In addition, an impact transmitted to the second impact blocking portion 412 may be absorbed by the impact absorbing member 42 and thus may be prevented from being transmitted to transducer module 23 through a side surface of the second impact blocking portion 412.

FIG. 9 and FIG. 10 are views illustrating a protective member according to another exemplary embodiment. FIG. 10 is an internal view illustrating an ultrasonic view including the protective member according to another exemplary embodiment.

Referring to FIGS. 9 and 10, an ultrasonic probe 2*a* according to another exemplary embodiment includes a protective member 5 capable of protecting a transducer module 23 from an external impact. The protective member 5 includes an impact blocking member 51 and an impact absorbing member 52.

The protective member 5 is positioned adjacent to at least one side surface of the transducer module 23. Similarly to the protective member 3 shown in FIGS. 4 and 5, the protective member 5 may be provided to further protrude by a certain height h compared to a front surface of the transducer module 23. Since the protective member 5 is provided at a higher level than the front surface of the transducer module 23, an external impact applied from in front of the transducer module 23 may be transmitted to the protective member 5 and may not be directly transmitted to the transducer module 23.

The impact blocking member 51 may be provided such that a concave portion 510 and a convex portion 511 are alternately formed. The concave portion 510 and the convex portion 511 may be provided to extend in a forward and backward direction of the transducer module 23. As described above, since the impact blocking member 51 is provided such that the concave portion 510 and the convex portion 511 are alternately formed, the impact blocking member 51 may have higher rigidity. Therefore, although a material having relatively low rigidity is used, the impact blocking member 51 may be designed to withstand required impulse due to a shape of the impact blocking member 51.

The impact absorbing member 52 may be positioned in a space formed by the shapes of the concave portion 510 and the convex portion 520 of the impact blocking member 51. The impact absorbing member 52 may be inserted into the space formed by the concave portion 510 and the convex portion 520 to absorb an impact transmitted to the impact blocking member 51. Therefore, an external impact may be prevented from being transmitted to the transducer module 23.

The shapes of the impact blocking member and the impact absorbing member capable of protecting the transducer module 23 from an external impact are not limited those described above.

The invention claimed is:

1. An ultrasonic probe comprising:
   a transducer module including a piezoelectric layer configured to generate an ultrasonic wave and an acoustic matching layer positioned to the front of the piezoelectric layer, the transducer module including an upper surface and a lower surface opposing each other in a stacking direction along which the piezoelectric layer and the acoustic matching layer are stacked, and a side surface connected directly to the upper surface and lower surface and extending in the stacking direction;
   a case which has an opened one side and is configured to accommodate the transducer module;
   a lens provided at the one side of the case; and
   a protective member accommodated in the case and positioned to face the side surface of the transducer module, wherein the protective member protrudes further forward compared to the acoustic matching layer so as to protect the transducer module from an external impact,
   wherein the protective member includes an impact blocking member and an impact absorbing member, the impact absorbing member being disposed between the impact blocking member and the transducer module to absorb an impact transmitted to the impact blocking member,
   wherein the impact blocking member and the impact absorbing member are provided to protrude forward from a side of the acoustic matching layer,
   wherein the side surface of the piezoelectric layer and the side surface of the acoustic matching layer are aligned on a same line,
   wherein among surfaces of the piezoelectric layer and the acoustic matching layer, the impact absorbing member extends linearly along the stacking direction and is disposed to cover only the side surfaces of the piezoelectric layer and the acoustic matching layer, and
   wherein the side surfaces of the piezoelectric layer and the acoustic matching layer are portions of the side surface of the transducer module.

2. The ultrasonic probe of claim 1, wherein the impact blocking member includes a first impact blocking portion and a second impact blocking portion extending in a stepped manner from the first impact blocking portion.

3. The ultrasonic probe of claim 2, wherein the impact absorbing member is positioned between the second impact blocking portion and the transducer module.

4. The ultrasonic probe of claim 2, wherein the second impact blocking portion extends forward from the first impact blocking portion.

5. The ultrasonic probe of claim 2, wherein a plurality of second impact blocking portions are provided to extend.

6. The ultrasonic probe of claim 5, wherein two second impact blocking portions are provided and positioned at a left side and a right side of the transducer module.

7. The ultrasonic probe of claim 6, wherein a length from one end of any one second impact blocking portion of the two second impact blocking portions to the other end of the other one is the same as a left-and-right length of the side surface of the transducer module.

8. The ultrasonic probe of claim 2, wherein a single second impact blocking portion is provided and extends forward in a stepped manner from the first impact blocking portion.

9. The ultrasonic probe of claim 8, wherein the impact absorbing member is positioned between the second impact blocking portion and the transducer module.

10. The ultrasonic probe of claim 1, wherein the impact blocking member is provided such that a concave portion and a convex portion are alternately formed.

11. The ultrasonic probe of claim 10, wherein the concave portion and the convex portion are provided to extend in a forward and backward direction of the transducer module.

12. The ultrasonic probe of claim 11, wherein the impact absorbing member is positioned in a space formed by the concave portion and the convex portion.

13. The ultrasonic probe of claim 1, wherein the impact absorbing member includes at least one selected from silicon rubber, polythene (PE), a polymer, an elastomer, and cellulose.

14. The ultrasonic probe of claim 1, wherein the impact blocking member is made of a metal or nonmetal material having a tensile modulus of 2 GPa or more.

15. The ultrasonic probe of claim 1, wherein the impact blocking member is spaced apart from the acoustic matching layer by the impact absorbing member disposed between the impact blocking member and the acoustic matching layer.

* * * * *